(12) United States Patent
Francke

(10) Patent No.: US 7,006,597 B2
(45) Date of Patent: *Feb. 28, 2006

(54) EXAMINATION METHOD AND APPARATUS

(75) Inventor: Tom Francke, Sollentuna (SE)

(73) Assignee: XCounter AB, Danderyd (SE)

( * ) Notice: Subject to any disclaimer, the term of this patent is extended or adjusted under 35 U.S.C. 154(b) by 44 days.

This patent is subject to a terminal disclaimer.

(21) Appl. No.: 10/750,948

(22) Filed: Jan. 5, 2004

(65) Prior Publication Data

US 2005/0119563 A1 Jun. 2, 2005

(30) Foreign Application Priority Data

Nov. 27, 2003 (SE) .................................. 0303177

(51) Int. Cl.
*G01B 15/02* (2006.01)

(52) U.S. Cl. .......................... 378/89; 378/156

(58) Field of Classification Search ................ 378/50, 378/51, 54, 62, 63, 64, 65, 86, 87, 89, 156, 378/157, 158, 159, 19; 250/374, 375; 600/431
See application file for complete search history.

(56) References Cited

U.S. PATENT DOCUMENTS

| | | | | |
|---|---|---|---|---|
| 4,536,790 A * | 8/1985 | Kruger et al. | ............. | 378/98.2 |
| 4,634,868 A | 1/1987 | DeLacy | ...................... | 250/306 |
| 5,236,693 A | 8/1993 | Lee | .............................. | 424/9.5 |
| 5,567,415 A | 10/1996 | Porter | ........................ | 424/9.52 |
| 5,772,984 A | 6/1998 | Berg et al. | ................. | 424/9.52 |
| 6,118,125 A | 9/2000 | Francke et al. | .......... | 250/385.1 |
| 6,337,482 B1 | 1/2002 | Francke | .................... | 250/385.1 |
| 6,373,065 B1 | 4/2002 | Francke et al. | ............. | 250/374 |
| 6,375,931 B1 | 4/2002 | Eriksen et al. | ............. | 424/9.52 |
| 6,385,282 B1 | 5/2002 | Francke et al. | ................ | 378/51 |
| 6,409,671 B1 | 6/2002 | Eriksen et al. | .............. | 600/458 |
| 6,414,317 B1 | 7/2002 | Francke et al. | .......... | 250/385.1 |
| 6,476,397 B1 | 11/2002 | Francke et al. | .......... | 250/385.1 |
| 6,477,223 B1 | 11/2002 | Francke | ....................... | 378/19 |
| 6,518,578 B1 | 2/2003 | Francke et al. | ............. | 250/374 |
| 6,522,722 B1 | 2/2003 | Francke | ..................... | 378/146 |
| 6,546,070 B1 | 4/2003 | Francke | ...................... | 378/51 |
| 6,547,738 B1 | 4/2003 | Lysyansky | .................. | 600/458 |
| 6,556,650 B1 | 4/2003 | Francke | ........................ | 378/62 |
| 6,595,925 B1 | 7/2003 | Eriksen et al. | ............. | 600/458 |
| 6,600,804 B1 | 7/2003 | Francke et al. | ................ | 378/51 |
| 6,627,897 B1 | 9/2003 | Francke et al. | .......... | 250/385.1 |
| 6,645,147 B1 | 11/2003 | Jackson et al. | ............. | 600/458 |
| 6,856,669 B1 * | 2/2005 | Francke et al. | ................ | 378/86 |

FOREIGN PATENT DOCUMENTS

EP 0782375 A1 7/1997

* cited by examiner

*Primary Examiner*—Edward J. Glick
*Assistant Examiner*—Courtney Thomas
(74) *Attorney, Agent, or Firm*—Harness, Dickey & Pierce, P.L.C.

(57) ABSTRACT

A method for examination of a subject comprises the steps of: administering (32) a contrast-enhancing agent into a subject (7, 42) to be examined, the contrast-enhancing agent introducing density variations in the subject; directing (33) ionizing radiation (3) towards the subject; and detecting (34) ionizing radiation spatially resolved as transmitted through the subject, while Compton scattered radiation (3a, 3c) in the subject is essentially prevented from being detected. The ionizing radiation directed towards the subject is provided within a spectral range so that more photons of the ionizing radiation are Compton scattered than absorbed through the photoelectric effect in the subject to thereby detect the density variations introduced by the contrast-enhancing agent in the subject spatially resolved.

30 Claims, 2 Drawing Sheets

EXAMINATION METHOD AND APPARATUS

FIELD OF THE INVENTION

The invention relates to a method and an apparatus for detection of ionizing radiation.

BACKGROUND OF THE INVENTION AND RELATED ART

Radiographic imaging detectors comprising an array of small sensors to capture a radiation-generated image are well known in the art. A collimated radiation beam is intensity modulated as it passes through a radiation-absorbing subject and the transmitted beam as detected thus represents an inverted image of the absorption by the subject, which in turn is related to the elemental composition, density, and thickness of the subject.

To improve contrast the broadband radiation from an X-ray tube is heavily filtered before being used for radiographic purposes. It is well known that at X-ray photon energies typically used, the photoelectric absorption is decreased as a power law as the X-ray photon energy increases, while unwanted scattering is increased.

For soft tissue the photoelectric absorption is decreasing rapidly at energies above about 20 keV and this higher energy X-ray radiation does not contribute to the image recorded, but reduces the contrast in the image. Thus, higher energies are filtered out from the radiation.

SUMMARY OF THE INVENTION

A problem with the known kind of approach is that most X-ray tubes have low efficiency at such low photon energy as 20 keV, i.e. the number of X-rays per unit power supplied to the tube is low.

Further, all X-ray tubes emit radiation within a wide energy spectrum. Typically, metallic foils filter the radiation from the X-ray tube, but simultaneously the flux of X-rays is reduced. Thus, large load has to be put on the X-ray tube to obtain a reasonable radiation flux downstream the metallic foils. Also, the relatively low flux affects the exposure time in an adverse manner, i.e. makes it long, which obviously limits the applicability of the technique.

Another issue of high importance is the radiation dose to the subject in case it is a living organism or part thereof. While the development of efficient collimators, appropriate filters, and sensitive detector arrays during the last decades have effectively reduced the radiation dose; still there is much to do. Further reduction of the radiation dose is a driving mechanism in detector design of today.

A main object of the invention is therefore to provide a method and an apparatus for examination of a subject, which overcome the above-identified problems as being related with the prior art.

In this respect there is a particular object to provide such a method and such an apparatus, which provide for the deposition of only small amounts of energy in a subject to be examined.

A further object of the invention is to provide such a method and such an apparatus, which provide for the possibility of using broadband radiation for the measurement.

A still further object of the invention is to provide such a method and such an apparatus, wherein radiation in a spectral range is used, in which the risk of under- or over exposing some areas of the image is reduced.

Yet a further object of the invention is to provide such a method and such an apparatus, wherein radiation over a wide energy range, and especially at high photon energies, can be detected with high efficiency.

These objects, among others, are attained by methods and apparatuses as claimed in the appended claims.

The inventors have found that by preventing Compton scattered radiation from being detected, and by providing ionizing radiation within a spectral range such that more, preferably much more photons, of the ionizing radiation are Compton scattered than absorbed through the photoelectric effect in the subject to be examined, an entirely new field of radiology opens up. Since the probability of scattering is essentially the same for a broad spectrum of photon energies, broadband radiation including higher energies can be used for the detection.

Variations in an image, captured at photon energies high enough to mainly obtain Compton scattering in the subject, are substantially due to the density only of the examined subject, provided that its thickness is constant, or known and corrected for. This is true since the attenuation coefficient for Compton scattering at photon energies of 10–300 keV is only weakly dependent on atomic number and photon energy. This is in sharp contrast to photoelectric absorption, which is heavily dependent on energy, and even more dependent on atomic number. Thus, the radiation image obtained is essentially a shadow image of the density variations in the subject to be examined.

In some radiographic applications, however, such as soft tissue applications including e.g. mammography, the density variations may be very small, and therefore the contrast in the recorded images is very low. According to the present invention, a suitable contrast-enhancing agent is therefore introduced into the subject to be examined. The suitable should modify the density of the subject to be examined and introduce density gradients into there. The density of the contrast-enhancing agent may be higher or lower than the density of the subject, but is preferably lower than the density of the subject. For instance, an ultrasound contrast agent may be employed. Contrast agents comprising or capable of generating dispersions of gas microbubbles are preferred, since such dispersions are particularly efficient due to the low density and ease of compressibility of the microbubbles. Thus, ordinary contrast enhancing agents for X-ray diagnostics, such as iodine, which introduce atomic number gradients into the subject rather than density gradients, are less suitable. Further, the ultrasound contrast agent administered to the subject should be sufficiently stable in vivo to be recirculated in the blood stream following administration, so that it may become equilibrated in the blood pool prior to imaging.

Preferably, Compton scattered radiation is prevented from being detected by means of a one-dimensional gas ionization detector including two electrodes, between which an ionizable gas is located, and a radiation entrance arranged such that said ionizing radiation enters said detector sideways between the electrodes, and electrons liberated by interaction between the ionizing radiation and the gas are accelerated in a direction essentially perpendicular thereto, wherein the distance between the electrodes is kept short to essentially only allow radiation collimated in a plane between the electrodes to ionize the gas. Further, the detector preferably employs electron avalanche amplification; wherein only radiation collimated in a very thin plane closest to the cathode electrode will be amplified sufficiently to essentially contribute to the signal as detected.

An advantage of the present invention is that if broadband radiation is used for the detection, there is less need of thick filters, the efficiency of the radiation source is increased, the load on the radiation source can be lowered, and the exposure time can be reduced due to the higher photon flux.

Further, since a scattered photon deposits only a fraction of its energy in a subject, whereas a photoelectrically absorbed photon deposits all its energy, the dose to the subject is reduced.

In a particular preferred embodiment of the present invention the above-mentioned novel examination method based on scattering rather than absorption, is combined with an ultrasound examination method. Here, the contrast-enhancing agent can be administered to the subject, after which the above-mentioned novel examination method based on scattering and the ultrasound examination method are performed, preferably simultaneously, using the same contrast-enhancing agent. This is particularly advantageous for mammography examinations, wherein the above-mentioned novel examination method based on scattering provides for the detection of a high-quality image of a breast to be examined causing an extremely low dose to the subject. For instance, the dose may be 20–100 times lower than in prior art X-ray mammography examinations. The ultrasound examination provides an ultrasound image, which serves as a complement for diagnosis. Some tumors will be better visualized in the ultrasound image.

Further characteristics of the invention, and advantages thereof, will be evident from the detailed description of preferred embodiments of the present invention given hereinafter and the accompanying FIGS. 1–4, which are given by way of illustration only, and thus are not limitative of the present invention.

DESCRIPTION OF PREFERRED EMBODIMENTS

Figure 1:
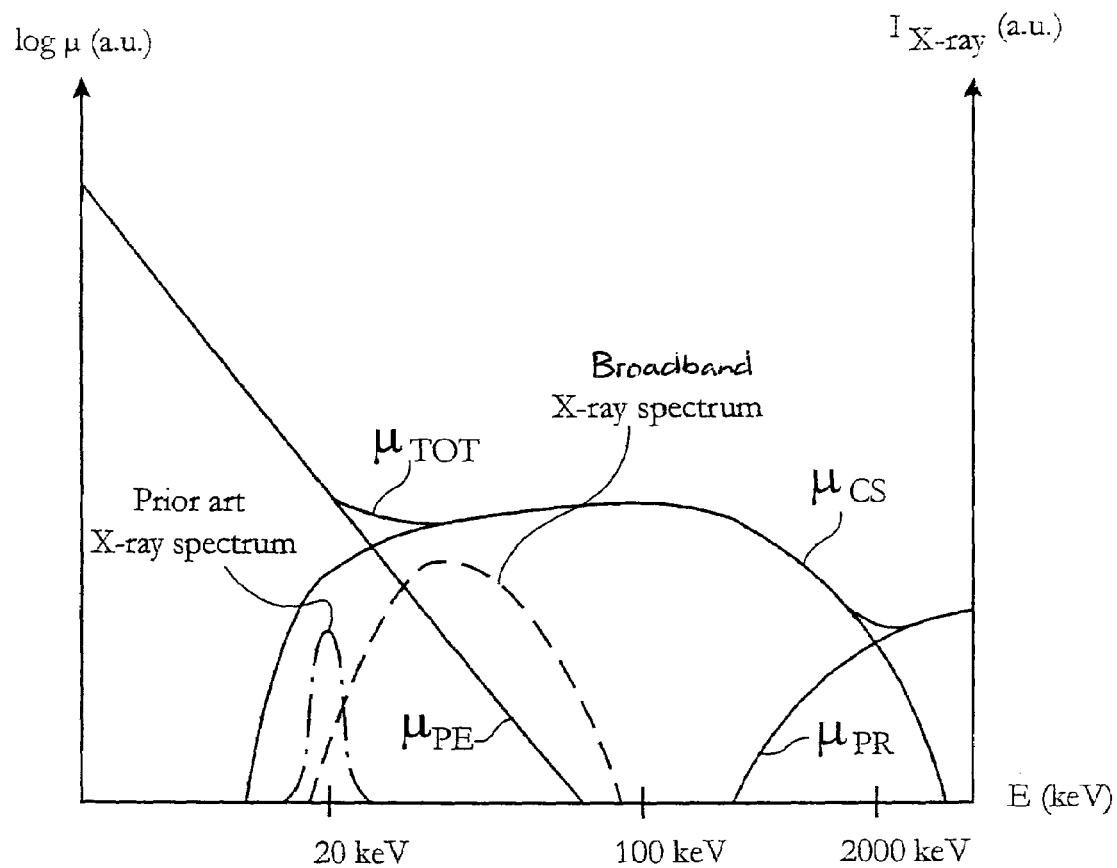
FIG. 1 is a schematic diagram illustrating photoelectric absorption, Compton scattering, pair production and total attenuation coefficients for human tissue as a function of X-ray photon energy, and a continuous X-ray spectrum of a typical X-ray source for use in the present invention.

As can be seen in FIG. 1, which is a schematic diagram illustrating photoelectric absorption, Compton scattering, pair production and total attenuation coefficient $\mu_{PE}$, $\mu_{CS}$, $\mu_{PR}$, $\mu_{TOT}$ for human soft tissue as a function of X-ray photon energy E, the photoelectric attenuation coefficient $\mu_{PE}$ decreases as a power law with photon energy, and at about 25 keV the Compton scattering attenuation coefficient $\mu_{CS}$ is comparable with the photoelectric absorption attenuation coefficient $\mu_{PE}$. Between about 30 and several hundred keV the Compton scattering attenuation coefficient $\mu_{CS}$ is completely dominating, whereas at higher photon energies (in the order of 1 MeV) the probability for pair production is increasing rapidly, and becomes the dominating interaction process. While FIG. 1 is illustrating an example only for human soft tissue, the relative overall structure of the diagram holds for a large variety of matter.

The Compton scattering attenuation coefficient $\mu_{CS}$ is fairly constant over a large range of photon energies. It can be seen in FIG. 1 the Compton scattering attenuation coefficient $\mu_{CS}$ for soft tissue is fairly constant between photon energies of about 30 and several hundred keV.

Further, the photoelectric absorption attenuation coefficient $\mu_{PE}$ is heavily dependent on the atomic number of the elements, of which the matter is comprised, whereas the Compton scattering attenuation coefficient $\mu_{CS}$ is only very weakly dependent on the atomic number.

Still further, the transmission through matter is dependent exponentially on the total attenuation coefficient $\mu_{TOT}$, on the density ρ of the matter, and on the thickness t of the matter according to:

$$\text{Transmission} \sim \exp[-(\mu_{TOT} * \rho * t)]$$

Thus, provided that ionizing radiation with photon energies high enough so that Compton scattering dominates over photoelectric absorption is passed through matter, the transmission through there is only very weakly dependent on atomic number of the matter, and the actual photon energy, but strongly dependent on the density of the matter. This is in sharp contrast to the case where photoelectric absorption is the dominating interaction mechanism. Here, the transmission through the matter is not only strongly dependent on the density of the matter, but also on the atomic number of the matter as well as on the actual photon energy employed. Thus, if ionizing radiation with photon energies high enough so that Compton scattering dominates over photoelectric absorption was used, it can be broadband radiation without having to perform complex calculations to compensate for any strong photon energy dependence.

A typical continuous X-ray spectrum from an 30 kV wolfram-based X-ray tube as filtered by a rhodium filter for use in e.g. mammography examinations according to prior art is schematically indicated in FIG. 1 by a dash-dotted line. Here, photoelectric absorption dominates over Compton scattering. A broadband X-ray spectrum from an 80 kV tungsten-based X-ray tube as filtered with a copper filter is indicated by a dashed line. The broadband radiation spectrum is displaced towards higher photon energies, at which Compton scattering dominates over photoelectric absorption.

Figure 2:
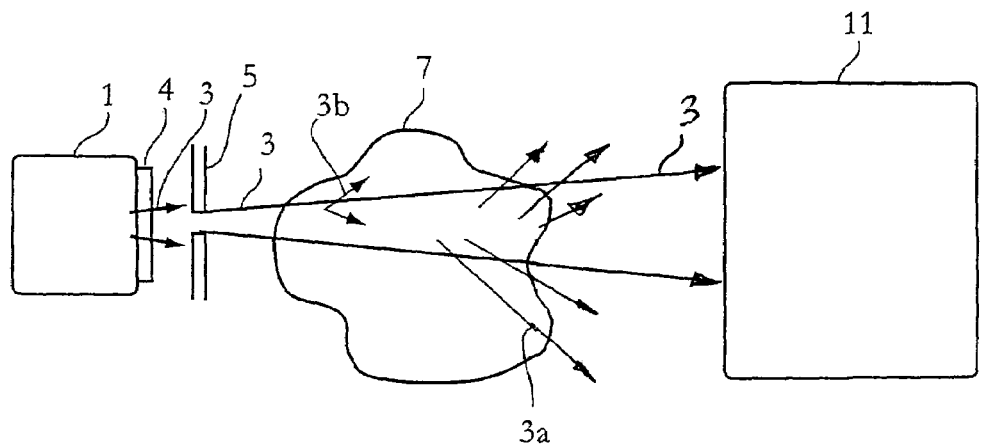
FIG. 2 illustrates schematically an apparatus for radiography used in the present invention.

FIG. 2 illustrates schematically, in a side elevation view, an apparatus for radiography for use in the present invention. The apparatus comprises, as seen from left to right, an X-ray source 1, a filter arrangement 4, an optional source aperture 5 and a detector device 11.

The X-ray source may be a tungsten-based X-ray tube emitting an X-ray radiation beam within a wide energy spectrum. The beam is filtered by means of the filter arrangement 4 at the output of the X-ray source 1. The filter arrangement 4 differs from a conventional filter in the sense that it transmits higher energies, and preferably a much wider spectrum, such as e.g. the broadband X-ray spectrum illustrated in FIG. 1. The radiation beam as filtered is subsequently passed through the optional source aperture 5 to collimate the beam. Preferably, the shape and size of the source aperture 5 is adapted to the particular size and kind of detector device 11. Thus, given a one-dimensional detector device, the aperture 5 is designed with a slit-shaped radiation transparent window, and given a rectangular two-dimensional detector device, the aperture 5 is preferably designed with a rectangular radiation transparent window.

The source collimator is optional and is used to reduce the dose to the subject to be examined in case the subject is a living organism or part thereof, by producing a beam of X-rays, which only illuminates the sensitive areas of the detector device 11.

The radiation beam 3 as filtered and optionally collimated enters a region, where a subject, subject-matter, matter, object or patient 7 to be imaged is located. In the subject 7 some photons may be photoelectrically absorbed, some may be Raleigh and Compton scattered (indicated by rays 3a in FIG. 1), and some photons may be converted into electrons and positrons in a pair production process, where these electrons and positrons may give rise to emission of X-ray photons (indicated by rays 3b in FIG. 1). The various processes depend on elemental composition of the subject 7 and on the photon energies of the incident radiation beam 3.

The radiation beam transmitted through the subject 7 without being deflected is detected by the detector device 11, while the scattered radiation is prevented from being detected. Typically, however, small amounts scattered radiation might enter into the detector device 11 and blur the image recorded.

According to the present invention the filter arrangement 4 is adapted to the elemental composition of the subject 7 to be imaged in a manner such the radiation beam as filtered is within a spectral range so that more photons of the radiation beam as filtered are Compton scattered than absorbed through the photoelectric effect in the subject 7, i.e. so that Compton scattering dominates over photoelectric absorption.

In the case of human soft tissue, such as breast tissue, the filtered radiation may be broadband X-ray radiation between 10 and 300 keV (i.e. similar to the broadband radiation spectrum of FIG. 1), preferably between 20 and 100 keV, and more preferably above 30 keV. In other applications the filtered radiation may be radiation above 30 keV.

Alternatively, the filtered radiation is in a spectral range such that at least 2 times, more preferably at least 5 times, and most preferably at least 10 times more photons of the filtered radiation are Compton scattered than absorbed through the photoelectric effect in the subject 7. If possible the filtered radiation should be in a spectral range, at which photoelectric absorption does not essentially occur in the subject 7.

The detector 11 has preferably an elongated opening for entry of the ionizing radiation; and a row of individual detector elements arranged essentially parallel with the elongated opening; and is of the kind wherein charges or photons generated by interactions between the ionizing radiation and a detection medium within the detector and travelling in a direction essentially perpendicular to the ionizing radiation, are detected by the row of individual detector elements.

The detector is preferably a gaseous-based parallel plate detector operating in avalanche amplification mode, wherein the signals in the individual detector elements originate essentially only from ionization within a thin layer, which may be at least 2–5 times thinner than the inter-plate distance. This advantageous behavior is obtained as the amplification is exponential and electrons liberated closer to the individual detector elements will not be able to produce signals strong enough.

For further details regarding different kind of detectors for use in the present invention, reference is made to the following U.S. patents by Tom Francke et al. and assigned to XCounter AB of Sweden, which patents are hereby incorporated by reference: U.S. Pat. Nos. 6,118,125; 6,373, 065; 6,337,482; 6,385,282; 6,414,317; 6,476,397; 6,477, 223; 6,518,578; 6,522,722; 6,546,070; 6,556,650; 6,600, 804; and 6,627,897.

Alternatively, the detector device 11 may more generally be any one- or two-dimensional detector, which is capable of discriminating scattered photons to a large extent. The detector may preferably any of a TFT-based detector; a scintillator-based detector; a solid state detector such as a CMOS- CCD-, CdZn- or CdZnTe-based detector; a gaseous-based detector; or a combination thereof, and is advantageously provided with an anti-scatter device, particularly an array of radiation-transparent channels arranged in front of the detector.

In order for the invention to operate properly, the scattered radiation has to be discriminated from being detected to an especially large extent. Preferably at least 90%, more preferably at least 99%, and most preferably at least 99.9% of the Compton scattered radiation in the subject 7 is prevented from being detected. The parallel plate detector described above has been shown to easily fulfill such a requirement.

By means of primarily using ionizing radiation at photon energies where Compton scattering dominates over photoelectric absorption, and by detecting the transmitted radiation separate from the radiation scattered in the subject, a number of advantages arise:

Since the radiation is primarily scattered off the subject 7 and not absorbed in it, the radiation dose to the subject is reduced. At photon energies of 50 keV a Compton scattered photon deposits only about 10% of the energy compared to a photoelectrically absorbed photon.

The filters may be made thinner since the radiation has not to be that heavily filtered (due to the Compton scattering attenuation coefficient compared to the photoelectric absorption attenuation coefficient). Less radiation is scattered in a thin filter than in a thick filter, which means that the scattered radiation from the filter arrangement 4 is reduced as compared with a conventional filter arrangement.

The efficiency of the X-ray tube is increased since larger portions of the emitted spectrum are usable. This means also that the load on the X-ray tube can be lowered. The exposure time can also be reduced due to the higher X-ray photon flux obtainable.

The attenuation coefficient for Compton scattering at photon energies of 10–300 keV is only weakly dependent on atomic number and photon energy, and thus variations in the image captured are essentially due to variations in the density of the subject only, provided that the subject thickness is constant, or known and corrected for.

The last advantage can in some applications be a drawback. If the density variations are very small as they can be in some mammography examinations the contrast in the image may be too low.

However, a solution to this comprises, in accordance with the present invention, to use a contrast-enhancing agent, which is suitable for the above-described X-ray imaging technique. The suitable contrast-enhancing agent should modify the density of the subject to be examined and introduce density gradients into there. For instance, an ultrasound contrast agent may be employed. Contrast agents comprising or capable of generating dispersions of gas microbubbles are preferred, since such dispersions are particularly efficient due to the low density and ease of compressibility of the microbubbles. Thus, ordinary contrast enhancing agents for X-ray diagnostics, such as iodine, which introduce atomic number gradients into the subject rather than density gradients, are less suitable. Further, the contrast agent administered to the subject should be sufficiently stable in vivo to be recirculated in the blood stream following administration, so that it may become equilibrated in the blood pool prior to imaging. Suitable contrast agents, which have been described for ultrasound examinations, and which are suitable in the present invention are disclosed in the U.S. Pat. Nos. 6,645,147; 6,595,925; 6,547,738; 6,409,671; 6,375,931; 5,772,984; 5,567,415; and 5,236,693, the contents of which being hereby incorporated by reference.

Figure 3:
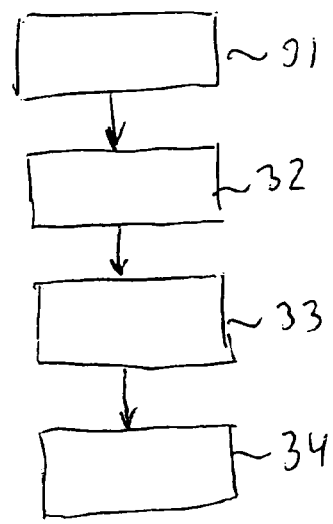
FIG. 3 is a flow diagram of a method according to a preferred embodiment of the present invention.

Thus, a method for examination of a subject according to a preferred embodiment of the invention, being illustrated in FIG. 3, comprises the following steps.

Ionizing radiation is provided, in a step 31, within a spectral range so that more photons of said ionizing radiation are Compton scattered than absorbed through the photoelectric effect in the subject to be examined. That is, the Compton scattering should be the dominating interaction mechanism of the interactions of the incident ionizing radiation with the subject. Preferably, the energy of the radiation photons should be selected so as to minimize the amount of photoelectric absorption in the subject given all other constraints, such as e.g. characteristics of the radiation source used, available radiation filters, required radiation flux, etc., as imposed by the particular application. Any of the radiation spectrum profiles disclosed in this description may be employed depending on the actual circumstances.

A suitable contrast-enhancing agent is, in a step 32, administered to the subject to be examined, where the contrast-enhancing agent introduces density variations in said subject. The contrast-enhancing agent may be any of the contrast-enhancing agents indicated above.

The ionizing radiation is then, in a step 33, directed towards and passed through the subject. In the subject, various interactions take place. However, the dominating interaction mechanism of the incident ionizing radiation with the subject is Compton scattering, which, as has been discussed above, is dependent on density, but fairly independent on atomic number and photon energy (within a given range).

The ionizing radiation as transmitted through said subject without being deflected is, in a step 34, detected spatially resolved, while the Compton scattered radiation in the subject is essentially prevented from being detected. For this purpose, any of the above-described scattering-rejection detecting apparatuses can be employed. If the photoelectric absorption can be neglected, the signals recorded can be arranged to form an image of the transmission, which would be a true inverted image, or shadow image, of the Compton scattering in the subject. Therefore, the image formed reveals spatially resolved density variations in the subject—density variations originally present in the subject as well as those introduced by the contrast-enhancing agent.

Figure 4:
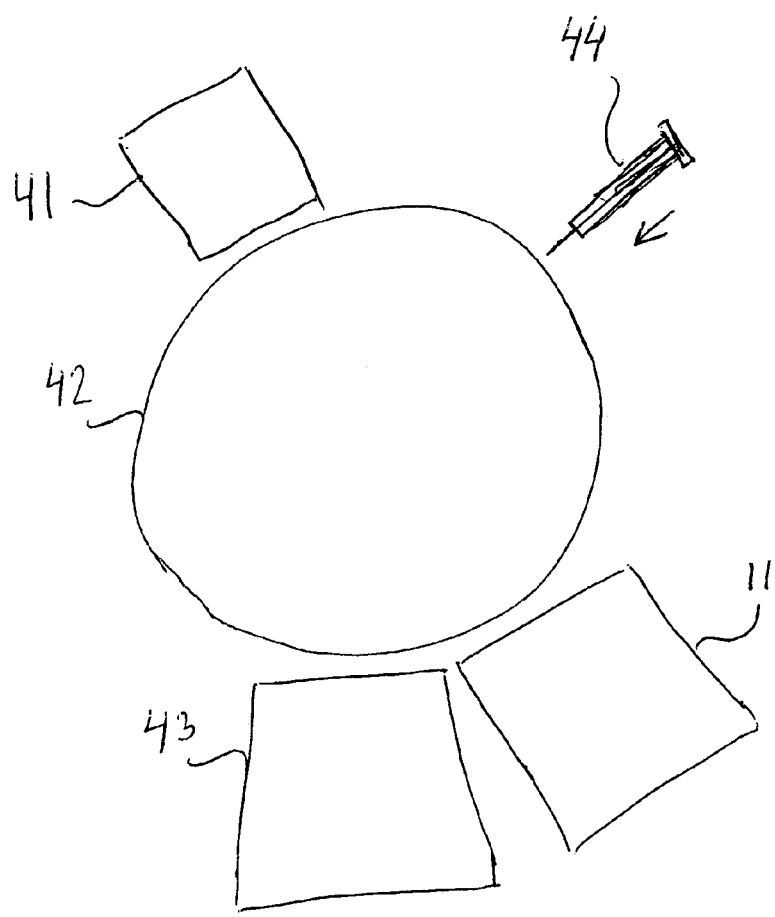
FIG. 4 illustrates schematically an apparatus for radiography according to another preferred embodiment of the present invention.

In a further preferred embodiment of the present invention, being illustrated in FIG. 4, the above-mentioned novel examination apparatus based on scattering rather than absorption, is combined with an ultrasound examination apparatus.

The X-ray detector device 11 and the X-ray source arrangement 41 including the X-ray source 1, the filter arrangement 4, and the optional source aperture 5 of FIG. 2, are arranged on opposite sides of a subject to be examined, such as a breast 42. An ultrasound examination apparatus 43 is arranged adjacent to the X-ray detector device 11. A device 44, such as a syringe, is provided for administering an ultrasound contrast-enhancing agent to the subject 42.

Prior to examination the ultrasound contrast-enhancing agent is administered to the subject 42, after which the breast is imaged, preferably simultaneously, by the X-ray detector device 11/X-ray source arrangement 41 combination and the ultrasound examination apparatus 43 using the very same contrast-enhancing agent administration.

This is particularly advantageous for mammography examinations, wherein the above-mentioned novel examination method based on scattering provides for the detection of a high-quality image of a breast of the subject to be examined, causing an extremely low dose to the subject. For instance, the dose may be 20–100 times lower than in prior art X-ray mammography examinations. The ultrasound examination provides an ultrasound image, which serves as a complement for diagnosis. Some tumors will be better visualized in the ultrasound image.

What is claimed is:

1. A method for examination of a subject comprising the steps of:
   administering a contrast-enhancing agent into a subject to be examined, said contrast-enhancing agent introducing density variations in said subject;
   directing ionizing radiation towards said subject; and
   detecting ionizing radiation spatially resolved as transmitted through said subject, while Compton scattered radiation in said subject is essentially prevented from being detected, wherein
   said ionizing radiation directed towards said subject is provided within a spectral range so that more photons of said ionizing radiation are Compton scattered than absorbed through the photoelectric effect in said subject to thereby detect the density variations introduced by the contrast-enhancing agent in said subject spatially resolved.

2. The method of claim 1 wherein said contrast-enhancing agent is a contrast agent for ultrasound examination.

3. The method of claim 2 wherein said contrast-enhancing agent comprises, or is capable of generating, dispersions of gas microbubbles.

4. The method of claim 2 wherein said method is combined with a spatially resolved ultrasound examination method, said spatially resolved ultrasound examination method being performed using said contrast-enhancing agent to thereby detect the density variations introduced by said contrast-enhancing agent in said subject spatially resolved also by said ultrasound examination method.

5. The method of claim 1 wherein said subject is human tissue, preferably a breast.

6. The method of claim 5 wherein said ionizing radiation is provided as broadband X-ray radiation between and 10 and 300 keV.

7. The method of claim 5 wherein said ionizing radiation is provided as broadband X-ray radiation between 20 and 100 keV.

8. The method of claim 5 wherein said ionizing radiation is provided as broadband X-ray radiation above 30 keV.

9. The method of claim 1 wherein said ionizing radiation is provided as radiation above 30 keV.

10. The method of claim 1 wherein said ionizing radiation is provided within a spectral range, at which photoelectric absorption does not essentially occur in said subject.

11. The method of claim 1 wherein said ionizing radiation is provided within a spectral range such that at least 2 times more photons of said ionizing radiation are Compton scattered than absorbed through the photoelectric effect in said subject.

12. The method of claim 1 wherein said ionizing radiation is provided within a spectral range such that at least 5 times more photons of said ionizing radiation are Compton scattered than absorbed through the photoelectric effect in said subject.

13. The method of claim 1 wherein said ionizing radiation is provided within a spectral range such that at least 10 times more photons of said ionizing radiation are Compton scattered than absorbed through the photoelectric effect in said subject.

14. The method of claim 1 wherein the step of detecting ionizing radiation spatially resolved as transmitted through said subject is performed by means of a gaseous-based parallel plate detector comprising an ionizable gas.

15. The method of claim 14 wherein electrons released as a result of ionization of said ionizable gas by said ionizing radiation are avalanche amplified before being detected.

16. An apparatus for radiographic examination of a subject comprising:
an X-ray source emitting broadband ionizing radiation;
a filter arrangement arranged in front of said X-ray source for filtering said emitted broadband ionizing radiation;
a subject region provided for housing said subject during said radiographic examination and arranged so that said filtered broadband ionizing radiation can be transmitted through said subject;
a device provided for administering a contrast-enhancement agent into said subject; and
a detector device arranged to record an image of said filtered broadband ionizing radiation as being transmitted through said subject, wherein
said filter arrangement has a filter function depending on the subject to be measured so that said ionizing radiation as filtered is within a spectral range so that more X-ray photons of said ionizing radiation are Compton scattered than absorbed through the photoelectric effect in said subject;
said device provided for administering a contrast-enhancement agent into said subject, is provided for administering a contrast-enhancement agent into said subject, which introduces density variations in said subject; and
said detector device is arranged to essentially prevent Compton scattered radiation in said subject from being detected.

17. The apparatus of claim 16 wherein said contrast-enhancing agent is a contrast agent for ultrasound examination.

18. The apparatus of claim 17 wherein said contrast-enhancing agent comprises, or is capable of generating, dispersions of gas microbubbles.

19. The apparatus of claim 17 further comprising a spatially resolved ultrasound examination apparatus, said spatially resolved ultrasound examination apparatus being provided to use said contrast-enhancing agent to thereby detect said density variations introduced by said contrast-enhancing agent in said subject spatially resolved.

20. The apparatus of claim 16 wherein said subject is human tissue.

21. The apparatus of claim 20 wherein said human tissue is a breast.

22. The apparatus of claim 16 wherein said filter arrangement has a filter function so that said ionizing radiation as filtered is provided within a spectral range such that at least 2 times more photons of said ionizing radiation are Compton scattered than absorbed through the photoelectric effect in said subject.

23. The apparatus of claim 16 wherein said filter arrangement has a filter function so that said ionizing radiation as filtered is provided within a spectral range such that at least 5 times more photons of said ionizing radiation are Compton scattered than absorbed through the photoelectric effect in said subject.

24. The apparatus of claim 16 wherein said filter arrangement has a filter function so that said ionizing radiation as filtered is provided within a spectral range such that at least 10 times more photons of said ionizing radiation are Compton scattered than absorbed through the photoelectric effect in said subject.

25. The apparatus of claim 16 wherein said detector device is a gaseous-based parallel plate detector comprising an ionizable gas.

26. The apparatus of claim 25 wherein said detector device is an electron avalanche detector, in which electrons released as a result of ionization of said ionizable gas by said ionizing radiation are avalanche amplified before being detected.

27. A method for examination of a subject comprising the steps of:
administering a contrast-enhancing gent into a subject to be examined, said contrast-enhancing agent introducing density variations in said subject;
directing ionizing radiation towards said subject; and
detecting ionizing radiation spatially resolved as transmitted through said subject, while Compton scattered radiation in said subject is essentially prevented from being detected, wherein
said ionizing radiation directed towards said subject is provided within a spectral range so that Compton scattering dominates over photoelectric effect in said subject to thereby detect the density variations introduced by the contrast-enhancing agent in said subject spatially resolved.

28. A method for examination of a subject comprising the steps of:
administering a contrast-enhancing agent into a subject to be examined, said contrast-enhancing agent introducing density variations in said subject;
directing ionizing radiation towards said subject; and
detecting ionizing radiation spatially resolved as transmitted through said subject, while a majority of the Compton scattered radiation in said subject is essentially prevented from being detected, wherein
said ionizing radiation directed towards said subject is provided within a spectral range depending on said subject to obtain Compton scattering as a dominating interaction mechanism between said ionizing radiation and said subject to thereby detect the density variations introduced by the contrast-enhancing agent in said subject spatially resolved.

29. An apparatus for radiographic examination of a subject comprising:
an X-ray source emitting broadband ionizing radiation;
a filter arrangement arranged in front of said X-ray source for filtering said emitted broadband ionizing radiation;
a subject region provided for housing said subject during said radiographic examination and arranged so that said filtered broadband ionizing radiation can be transmitted through said subject;
a device provided for administering a contrast-enhancement agent into said subject; and
a detector device arranged to record an image of said filtered broadband ionizing radiation as being transmitted through said subject, wherein said filter arrangement has a filter function depending on the subject to be measured so that said ionizing radiation as filtered is within a spectral range so that Compton scattering dominates over photoelectric effect in said subject;

said device provided for administering a contrast-enhancement agent into said subject, is provided for administering a contrast-enhancement agent into said subject, which introduces density variations in said subject; and said detector device is arranged to prevent the majority of Compton scattered radiation in said subject from being detected.

30. An apparatus for radiographic examination of a subject comprising:

an X-ray source emitting broadband ionizing radiation;

a filter arrangement arranged in front of said X-ray source for filtering said emitted broadband ionizing radiation;

a subject region provided for housing said subject during said radiographic examination and arranged so that said filtered broadband ionizing radiation can be transmitted through said subject;

a device provided for administering a contrast-enhancement agent into said subject; and a detector device arranged to record an image of said filtered broadband ionizing radiation as being transmitted through said subject, wherein said filter arrangement has a filter function depending on the subject to be measured so that said ionizing radiation as filtered is within a spectral range to obtain Compton scattering as a dominating interaction mechanism between said ionizing radiation and said subject;

said device provided for administering a contrast-enhancement agent into said subject, is provided for administering a contrast-enhancement agent into said subject, which introduces density variations in said subject; and said detector device is arranged to essentially prevent the Compton scattered radiation in said subject from being detected.

* * * * *